United States Patent [19]

Nunokawa

[11] 4,435,051
[45] Mar. 6, 1984

[54] WORKING DISTANCE DETECTING DEVICE FOR OPHTHALMIC APPARATUS

[75] Inventor: Kazuo Nunokawa, Itabashi, Japan

[73] Assignee: Tokyo Kogaku Kikai Kabushiki Kaisha, Japan

[21] Appl. No.: 269,670

[22] Filed: Jun. 3, 1981

[30] Foreign Application Priority Data

Jun. 10, 1980 [JP] Japan ................. 55-77935

[51] Int. Cl.³ ............... A61B 3/14; G03B 29/00
[52] U.S. Cl. ........................ 351/208; 354/62
[58] Field of Search .......................... 351/208; 354/62

[56] References Cited

U.S. PATENT DOCUMENTS 4,219,258 8/1980 Araki ........................... 354/62
4,257,687 3/1981 Kohayakawa ..................... 351/206

FOREIGN PATENT DOCUMENTS 54-9489 1/1979 Japan .
54-42895 4/1979 Japan .
54-42896 4/1979 Japan .
54-15487 12/1979 Japan .

Primary Examiner—John K. Corbin
Assistant Examiner—Rodney B. Bovernick
Attorney, Agent, or Firm—Brumbaugh, Graves, Donohue & Raymond

[57] ABSTRACT

An eye fundus camera is disclosed having a working distance detecting device. The eye fundus camera includes an illuminating system having a ring-shaped aperture through which the illuminating light beam is projected to the eye to be examined through an objective lens. The working distance detecting device includes an opaque portion formed in said ring-shaped aperture and having a width in circumferential direction. A light receiving portion is provided around the objective lens at a position corresponding to the opaque portion in the image of the ring-shaped aperture formed by beams of the illuminating light reflected from the cornea of the eye so that the working distance can be detected based on the width of the opaque portion of the image of the ring-shaped aperture.

5 Claims, 7 Drawing Figures

WORKING DISTANCE DETECTING DEVICE FOR OPHTHALMIC APPARATUS

BACKGROUND OF THE INVENTION

The present invention relates to a working distance detecting device in an ophthalmic apparatus.

In an ophthalmic apparatus such as a funduscopic camera, illuminating beams are projected on an eye to be examined through an object lens confronting to the eye to be examined, and in case of an eye fundus camera, an arrangement is made such that reflected beams of the projected light from the fundus are guided to a photographic optical system. In such eye fundus cameras as well as other ophthalmic apparatus in which illuminating beams are projected on an eye to be examined through an object lens and a flux of beams reflected from the interior of the eye to be examined is guided to a photographic optical system or an observation optical system, there is a risk of occurrence of a flare or ghost because of intrusion of illuminating beams reflected from the face of the cornea of the eye being examined, into the photographic or observation optical system.

As means for overcoming this problem of occurrence of a flare or ghost by a flux of reflected beams of illuminating light, conventional apparatus include an illuminating optical system which has an annular or ring-shaped aperture and an apertured mirror slantingly disposed along the optical axis of the object lens at a position substantially conjugate to the pupil of an eye to be examined with respect to the object lens so that a ring-shaped flux of illuminating beams passing through the ring-shaped aperture is once focussed on an annular reflection surface of the apertured mirror and the flux is then made incident into the eyeball through the pupil of the eye being examined from the object lens. If this arrangement is adopted, occurrence of a flare or ghost due to reflection of illuminating beams on the cornea can be prevented when the perforated mirror is located at a position substantially conjugate to the pupil of the eye to be examined with respect to the object lens. More specifically, since the distance between the object lens and the apertured mirror is always constant, when the distance between the object lens and the eye to be examined, that is, the working distance, is appropriate, occurrence of a flare or ghost can be prevented.

Accordingly, in an ophthalmic apparatus of this type, it is very important to maintain an appropriate working distance while the apparatus is used. This appropriate working distance has heretofore been obtained by precisely moving the apparatus by an operator while observing a picture image produced in an observation optical system, that is, a picture image produced on a Braun tube of a monitor television when illuminating beams are infrared rays or a picture image seen through an eye lens when illuminating beams are visible rays. When this conventional method is adopted, since not only this operation of adjusting the working distance but also other complicated operations such as adjustment of alignment of the optical axis of the object lens with the eye to be examined and the focusing should simultaneously be performed, a certain degree of flare or ghost is apt to be overlooked. Furthermore, in an ophthalmic apparatus of the type where the operation of alignment adjustment and the focussing operation are carried out by using infrared rays, it is very difficult to detect rays diffused on the cornea or the crystalline lens on a Braun tube of a television.

As means for eliminating this disadvantage, a proposal has been made by Japanese Patent Application No. 81631/79. According to this proposal, a light-receiving portion is disposed in the peripheral region of the object lens and the working distance is detected in terms of the position of the flux of beams reflected from the cornea on this light-receiving portion. The light-receiving portion may be constructed, for example, by a light-receiving plate arranged coaxially with the object lens in the peripheral region of the object lens. In this case, when the radius of the inner circumference of an image of illuminating beams reflected from the cornea, which is formed on the surface of the light-receiving plate, has a predetermined value, it is judged that the working distance is appropriate. Furthermore, the state of alignment of the object lens with an eye to be examined can be known by examining whether or not the inner circumference of the image formed on the surface of the light-receiving plate is coaxial with the optical axis of the object lens.

This working distance detecting device is very advantageous over the conventional ones because the working distance and the alignment can be detected very conveniently. Furthermore, if an optical fiber or photoelectric element is used instead of the light-receiving plate, any necessary display can easily be accomplished on an image forming portion of the observation optical system. However, in this device, since both the working distance and the alignment are detected only by detecting the position of the inner circumference of the image of the ring-shaped aperture formed by beams reflected at the cornea of the eye, actual adjustment involves some problem or difficulties.

SUMMARY OF THE INVENTION

It is a primary object of the present invention to provide a device for detecting an working distance by using an annular or ring-shaped aperture image formed by beams reflected at the cornea of an eye to be examined, in which the working distance is detected by using information different from the information used for detection of the alignment.

According to the present invention, the above and other objects can be accomplished by an opthalmic apparatus which comprises objective lens means adapted to be located opposite an eye to be examined with a working distance, an illuminating optical system having a ring-shaped aperture located substantially conjugate to the cornea of the eye with respect to the objective lens means so that a beam of illuminating light is projected on the eye through said aperture and said objective lens means from said slit, a working distance detecting device which comprises at least one light-shading opaque portion provided in said aperture and having a width in circumferential direction and light-receiving means provided around said objective lens means at a position corresponding to said light-shading opaque portion in a ring-shaped aperture image formed by the illuminating beam reflected from the cornea of the eye to be examined, whereby the working distance between the objective lens means and the cornea of the eye is detected based on the width of the light-shading opaque portion in the aperture image detected by said light-receiving portion.

According to the features of the present invention, the working distance between the objective lens and the eye to be examined is detected by the width of the image of the light-shading opaque portion in the ring-shaped aperture, formed by the light beam reflected at the cornea of the eye to be examined, and if necessary, the alignment is judged according to the positional relationship between the inner circumference of the image of the aperture and the objective lens. Therefore, these detecting operations can be performed very easily and occurrence of an erroneous operation can be prevented satisfactorily. In order to detect the position of the inner circumference of the aperture image, it may be preferable to provide a second light receiving portion around the objective lens.

BRIEF DESCRIPTION OF THE DRAWINGS

The above and other objects and features of the present invention will become apparent from the following description of a preferred embodiment taking reference to the accompanying drawings, in which.

DETAILED DESCRIPTION OF THE PREFERRED EMBODIMENTS

Figure 1:
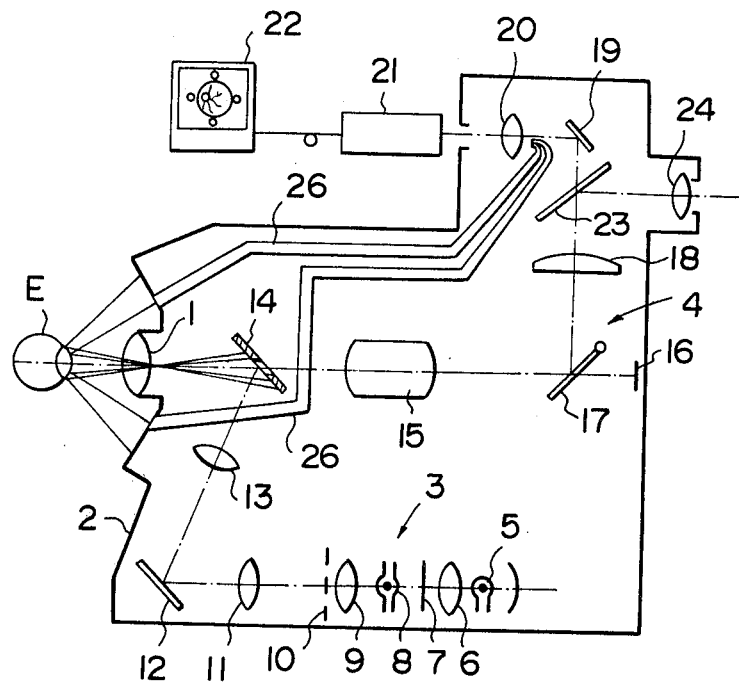
FIG. 1 is a view diagrammatically illustrating one embodiment of the present invention in which the present invention is applied to an eye fundus camera.

Referring now to the drawings, FIG. 1 illustrates an embodiment in which the present invention is applied to an eye fundus camera. This eye fundus camera comprises an objective lens 1 opposite to an eye E to be examined, and an illuminating optical system 3 and an observation or photographic optical system 4 which are contained in a housing 2. The illuminating optical system 3 comprises an illuminating light source 5 for observation and a photographic light source 8, such as a stroboscopic tube, which is arranged to confront the light source 5 through a condenser lens 6 and a red filter 7. Beams from these light sources are converged by a condenser lens 9 and are focused in the form of an annular image on the reflection face of an apertured mirror 14 slantingly disposed on the optical axis of the objective lens 1 through a relay lens 11, a reflecting mirror 12 and a relay lens 13 from a ring-shaped aperture 10. The beams are reflected from the reflection face of the perforated mirror 14 toward the objective lens 1 and are projected on the eye E to be examined through the objective lens 1.

The beams reflected from the fundus of the eye E are made incident on the eye fundus camera through the objective lens 1 and passed through the central aperture of the mirror 14 to be made incident on the observation or photographic optical system 4. The observation optical system 4 has an image forming lens 15 and beams which have passed through this image forming lens 15 are focussed in the form of an image on the surface of a photographic film 16. A mirror 17 is slantingly disposed in front of the surface of the photographic film 16 in such a manner that the mirror 17 can be sprung up during the photographing operation. The beams reflected from the mirror 17 are focussed on the focussing surface of a field lens 18, and the beams passing through the field lens 18 are reflected by a reflecting mirror 19 and focussed on the photoelectric surface of a pickup tube 21 through an image forming lens 20. Signals from the pickup tube 21 are transmitted to a monitor television 22 to form a picture image on the screen of a Braun tube. Another mirror 23 is slantingly disposed between the field lens 18 and mirror 19, and the beams reflected at this mirror 23 are observed through an eye lens 24. The mirror 23 may be disposed on that the mirror 23 is optionally retreated from an observation optical path.

Figure 2:
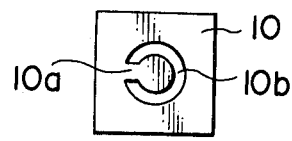
FIG. 2 is a front view illustrating one example of the ring-shaped aperture.
Figure 3:
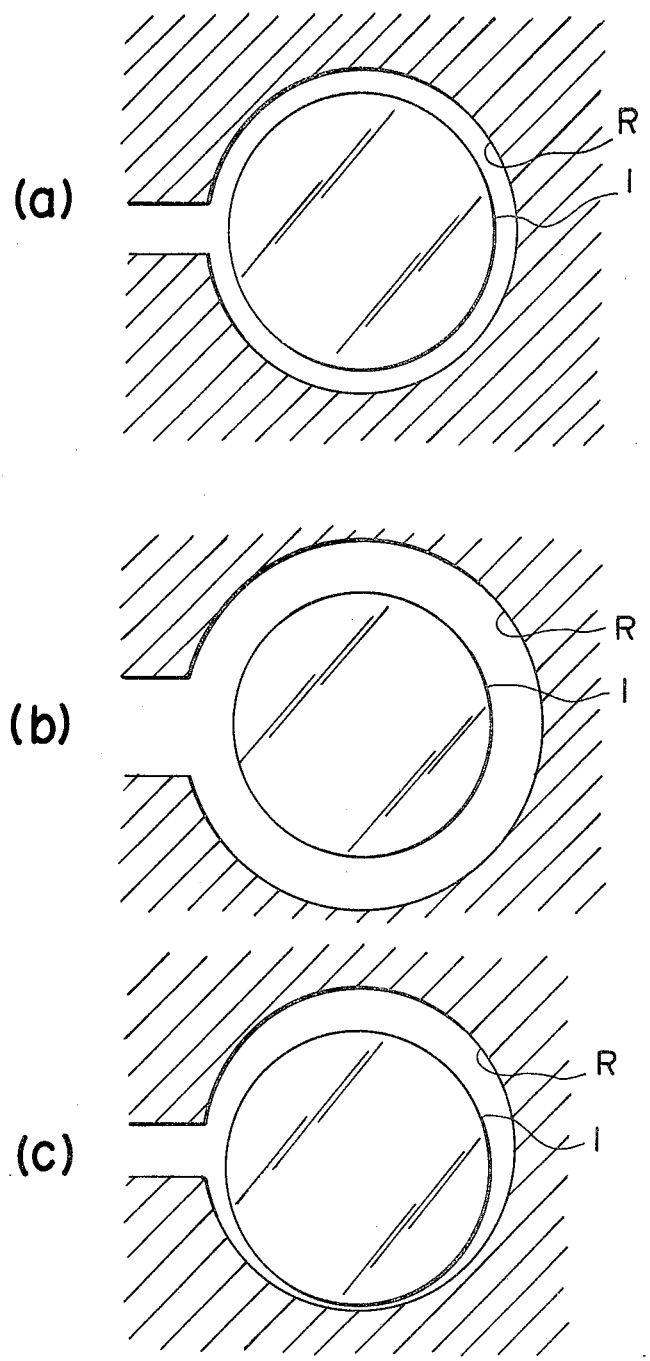
FIGS. 3(a) through (c) show the positional relationship between the objective lens and the aperture image reflected at the cornea.

The annular aperture 10 is not a complete ring-like shape but it consists of a substantially C-shaped transmitting portion 10b including a light-shading opaque portion 10a having a certain width in the circumferential direction, as shown in FIG. 2. A part of the flux of beams projected on the eye E through the objective lens 1 is reflected on the face of the cornea of the eye to form an image of the aperture 10 in the peripheral region of the objective lens 1. This image as represented by symbol R in FIG. 3-A is coaxial with the objective lens 1 when an appropriate working distance is maintained between the objective lens 1 and the eye E to be examined and also an appropriate alignment is kept, and in this case, the radius of the inner circumference of the annular slit image has a predetermined value and the width of the portion corresponding to the light-shading opaque portion 10a has a predetermined value. In contrast, when the working distance is too short, as shown in FIG. 3-B, the radius of the inner circumference of the aperture image R is larger than the predetermined value and also the width of the portion corresponding to the light-shading opaque portion 10a is larger than the predetermined value. If the alignment is not appropriate, as shown in FIG. 3-C, the annular aperture image R is not coaxial with the objective lens 1.

Figure 4:
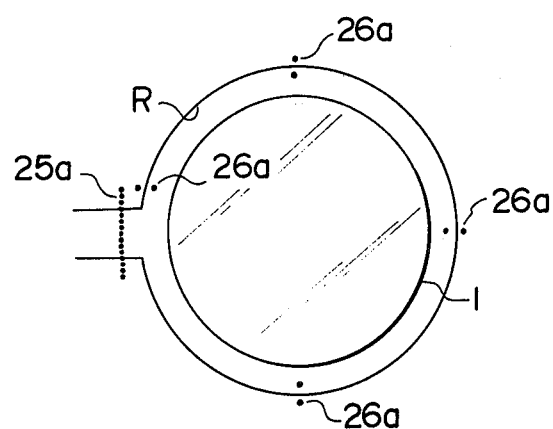
FIG. 4 is a view showing an example of the light-receiving portion.

For detecting such changes of the aperture image, optical fibers 25 and 26 are provided as shown in FIG. 4 so that light-receiving portion be formed by the ends 25a and 26a thereof. A first light-receiving portion is constituted by the ends 25a of the optical fibers 25 arranged in a row traversing the image of the light-shading opaque portion 10a in the direction of the width, and a second light-receiving portion by the ends 26a of a plurality pairs of optical fibers 26 which are arranged on the same circular line, so that when the working distance and alignment are appropriate, the inner circumference of the annular slit image R is interposed between each paired optical fiber ends 26a. The angle between every two adjoining pairs of the optical fibers 26 is 90°. The other ends 25b and 26b of the optical fibers 25 and 26 are arranged on the front side of the image forming lens 20 so that beams passing through these ends 25b and 26b are sensed by the pickup tube 21 to form images on the television 22.

Figure 5:
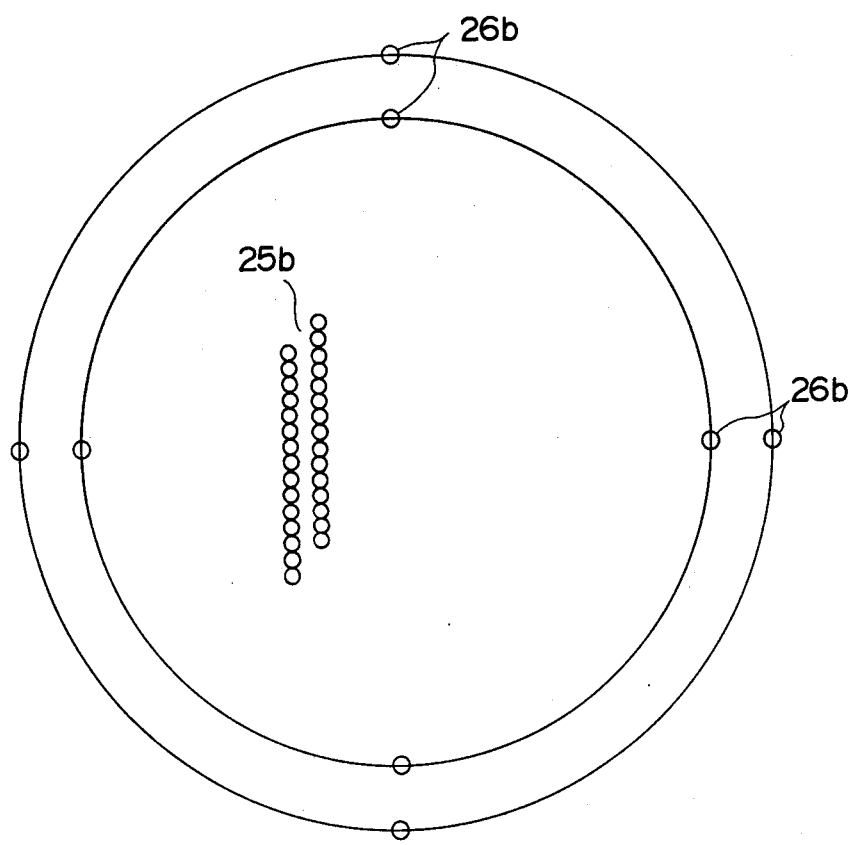
FIG. 5 is a view showing an example of the arrangement in the observation section.

In connection with the arrangement of the fiber ends 25b, it is preferred that a row of fiber ends 25b corresponding to the fiber ends 25a be divided into two segments and appropriate numbers of corresponding fiber ends 25b of the respective segments be overlapped to each other, as shown in FIG. 5. Of course, other arrangements may optionally be adopted. The paired fiber ends 26b may be arranged on the same circles so that the angular interval between every two adjacent pairs of the fiber ends 26b is 90°, as shown in FIG. 5. Of course, photoelectric elements and the like may be used as the detecting means instead of such optical fibers.

The invention has thus been shown and described with reference to a specific embodiment; however, it should be noted that the invention is in no way limited to the details of the illustrated arrangements, but changes and modifications may be made without departing from the scope of the appended claims.

I claim:

1. An ophthlamic apparatus which comprises objective lens means adapted to be located opposite an eye to be examined with a working distance therebetween, an illuminating optical system having a ring-shaped aperture located substantially conjugate to the cornea of the eye with respect to the objective lens means so that a beam of illuminating light is projected on the eye through said aperture and said objective lens means, a working distance detecting device which comprises at least one light-shading opaque portion provided in said aperture and having a width in a circumferential direction and light-receiving means provided outside the perimeter of said objective lens means at a position capable of receiving a projection of said light-shading opaque portion of the ring-shaped aperture by the illuminating beam reflected at the cornea of the eye to be examined, whereby the working distance between the objective lens means and the cornea of the eye is detected based on the width of the projection of the light-shading opaque portion onto said light-receiving means.

2. An ophthalmic apparatus in accordance with claim 1 which further includes second light receiving means around said objective lens means for detecting an inner circumference of the image of the ring-shaped aperture to thereby detect an alignment of the eye with the objective lens means.

3. An opthalmic apparatus in accordance with claim 1 in which said light-receiving means is a planar surface provided around the objective lens means.

4. An ophthalmic apparatus in accordance with claim 1 in which said light receiving means is constituted by one end of optical fibers arranged in at least one row in a direction to widthwisely traverse the projection of the opaque portion, the other end of the optical fibers being in an observing optical system of the apparatus.

5. An ophthalmic apparatus in accordance with claim 2, in which said light receiving means is constituted by one end of optical fibers arranged in at least one row in a direction of widthwisely traverse the image of the opaque portion, said second light receiving means is constituted by a plurality of pairs of one end of said optical fibers with said pairs being arranged along a circle coaxial with the objective lens means with one end of each pair being radially inside said circle and another end of each pair radially outside said circle, the other ends of the optical fibers being in an observing optical system of the apparatus.

* * * * *